United States Patent [19]

Watson

[11] 4,341,600
[45] Jul. 27, 1982

[54] POLYMERIZATION INHIBITOR FOR VINYLTOLUENE

[75] Inventor: James M. Watson, Big Spring, Tex.

[73] Assignee: Cosden Technology, Inc., Dallas, Tex.

[21] Appl. No.: 251,368

[22] Filed: Apr. 6, 1981

[51] Int. Cl.³ .............................................. B01D 3/34
[52] U.S. Cl. ......................................... 203/9; 203/56;
585/808; 585/833; 585/865; 585/952
[58] Field of Search ............... 585/807, 808, 833, 834,
585/864, 865, 950, 952; 208/347; 203/6, 8, 9,
51, 56, 59, 65

[56] References Cited

U.S. PATENT DOCUMENTS 3,988,212 10/1976 Watson ................................... 203/9
4,182,658 1/1980 Watson ................................... 203/9

Primary Examiner—Frank Sever
Attorney, Agent, or Firm—M. Norwood Cheairs; J. D. Evans

[57] ABSTRACT

A process for distilling vinyltoluene comprising subjecting vinyltoluene to distillation conditions in the presence of a synergistic polymerization inhibiting mixture of N-nitrosodiphenylamine (NDPA) and dinitro-para-cresol (DNPC). Preferably from about 100 to about 300 ppm by weight NDPA and about 300 to about 700 ppm by weight DNPC are dissolved in the crude vinyltoluene and the resulting solution is vacuum distilled.

6 Claims, 2 Drawing Figures

POLYMERIZATION INHIBITOR FOR VINYLTOLUENE

BACKGROUND OF THE INVENTION

The present invention relates to a process for the distillation of readily polymerizable vinyltoluene. More particularly, the present invention relates to a process for the distillation of vinyltoluene wherein the amount of said materials polymerized during distillation over an extended period of time is reduced.

It is well known that vinyltoluene polymerizes very readily, and furthermore, that the rate of polymerization increases at elevated temperatures. Since vinyltoluene produced by common industrial methods contains impurities, the vinyltoluene must be subjected to separation and purification processes in order to be suitable for most types of further industrial use. Such separation and purification is generally accomplished by distillation.

In order to prevent polymerization during distillation of vinyltoluene, various types of known polymerization inhibitors have been employed in connection with prior art distillation processes. Only a very few of these compounds have proved to be of any utility for inhibiting vinyltoluene polymerization under distillation conditions and even fewer are effective in the columns of the distillation apparatus.

In a typical distillation process for vinyltoluene, utilizing a polymerization inhibitor, the mixture of material to be distilled is generally contacted with the chemical polymerization inhibitor prior to distillation in the distillation apparatus. It remains as a significant problem today that the amount of polymer formed in the distillation apparatus is substantially higher than desired. Occasionally, polymer deposits accumulate inside the distillation apparatus until portions of the apparatus may become plugged or blocked.

Accordingly, there exists a strong need for a polymerization inhibitor which will effectively prevent the polymerization of vinyltoluene during distillation.

SUMMARY OF THE INVENTION

It is therefore an object of the present invention to provide an improved process for the distillation of readily polymerizable vinyltoluene.

A further object of the present invention is to provide an improved process for the distillation of readily polymerizable vinyltoluene which process results in increased recovery of high purity vinyltoluene and concomitantly in a decrease in the production of less desirable by-product tars.

A further object of the invention resides in the provision of an improved process for the distillation of vinyltoluene which results in the production of substantially less polymerized material in the distillation apparatus.

It is also an object of the present invention to provide an improved process for the distillation of vinyltoluene which permits the distillation apparatus to be operated at an increased rate of throughput without a reduction of efficiency.

It is still a further object of the present invention to provide an improved process for the distillation of vinyltoluene which provides all of the foregoing enumerated advantages in a vacuum distillation system.

A specific object of the invention resides in the provision of a new and improved polymerization inhibitor system for use in the distillation of vinyltoluene.

In accomplishing the foregoing and other objects, there has been provided in accordance with the present invention a process for the distillation of vinyltoluene comprising subjecting the vinyltoluene to distillation conditions in a distillation system in the presence of an inhibitor system which comprises a mixture of N-nitrosodiphenylamine (NDPA) and dinitro-p-cresol (DNPC). Both NDPA and DNPC are soluble in vinyltoluene. Preferably, the distillation is a vacuum distillation.

In one aspect of the process according to the invention, the NDPA-DNPC inhibitor mixture is simply introduced into the distillation system by adding it to the reboiler of the benzene-toluene column. In a second aspect of the invention, the NDPA-DNPC inhibitor mixture is added to the feed of the recycle column. Alternatively, in a third preferred aspect of the invention, the NDPA-DNPC inhibitor mixture is added by incorporating it into the incoming stream of vinyltoluene to be purified. The amount of the inhibitor mixture necessary to effectively inhibit polymerization of vinyltoluene may vary over a wide range depending upon various factors of the distillation process, e.g., temperature, reflux ratio, pressure, residence time, etc. Typically, however, it has been found that an amount of the inhibitor mixture between about 50 and 3000 ppm, and preferably 200 to 1000 ppm, is sufficient to inhibit polymerization of vinyltoluene under normal distillation conditions (105° C.).

Dinitro-para-cresol inhibits polymerization of vinyltoluene liquids, but alone it is not effective in vapor spaces of the distillation apparatus or in overhead liquids because it is not volatile under the conditions encountered in the distillation apparatus. N-nitrosodiphenylamine slowly decomposes and evolves nitric oxide (NO) gas which inhibits polymerization of vinyltoluene, but when used alone it also fails to provide effective protection against formation of undesired polymer during distillation of vinyltoluene. When the two substances are used in combination, however, effective protection against formation of undesired polymer material is obtained throughout the distillation of vinyltoluene. The resulting effect is synergistic, i.e., the resulting inhibiting effect when the two substances are used in combination is substantially greater than the sum of the effects when the substances are used separately. Moreover, formation of undesired polymer is effectively inhibited without contamination of the desired vinyltoluene monomer product.

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Also, the present inhibitor mixture is found to produce a synergistic effect when compared to the inhibiting activity of either of the components alone.

Other objects, features and advantages of the invention will become apparent from the detailed description of the preferred embodiments which follows.

DETAILED DESCRIPTION OF PREFERRED EMBODIMENTS

The distillation process of the present invention employs an inhibitor system made up of a mixture of N-nitrosodiphenylamine and a dinitro-p-cresol as the polymerization inhibitor during the distillation of vinyltoluene. Typically, the distillation process is carried out under reduced pressure, e.g., vacuum distillation.

While DNPC alone is relatively effective in decreasing polymerization of the liquid crude vinyltoluene, it is not volatile under the conditions maintained in the distillation apparatus and therefore it is not effective in providing vapor space protection in the distillation apparatus. However, it has been found that NDPA, in combination with DNPC, is effective in greatly reducing polymerization in the distillation train. NDPA is believed to be a particularly effective synergistic inhibitor because of its slow evolution of NO gas under distillation conditions.

The mixture of NDPA and DNPC employed as the inhibitor system of the present invention generally contains 10 to 90% by weight of NDPA with the remainder being DNPC. Preferably, however, the amount of NDPA will be within the range of about 25 to 75% with the remainder being DNPC.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 ppm and about 3000 ppm by weight have generally provided suitable results, depending primarily upon the temperature of the distillation mixture and the degree of inhibition desired. More often, however, with the inhibitor system of the present invention, the NDPA-DNPC mixture is used in concentrations of 200 to 1000 ppm.

The crude vinyltoluene mixture is fractionally distilled in a series of fractionating columns. The distillation is preferably conducted under reduced pressure to further reduce the tendency of the vinyltoluene to polymerize. Lower boiling portions are separated from the vinyltoluene. The vinyltoluene is then removed from the heavier boiling fractions. Typical operating conditions for the distillation process include a temperature from about 65° to about 138° C., and at a subatmospheric pressure from about 10 to about 200 mm Hg absolute. The specific operation conditions produce a final vinyltoluene product of commercially acceptable quality and purity.

Figure 1:
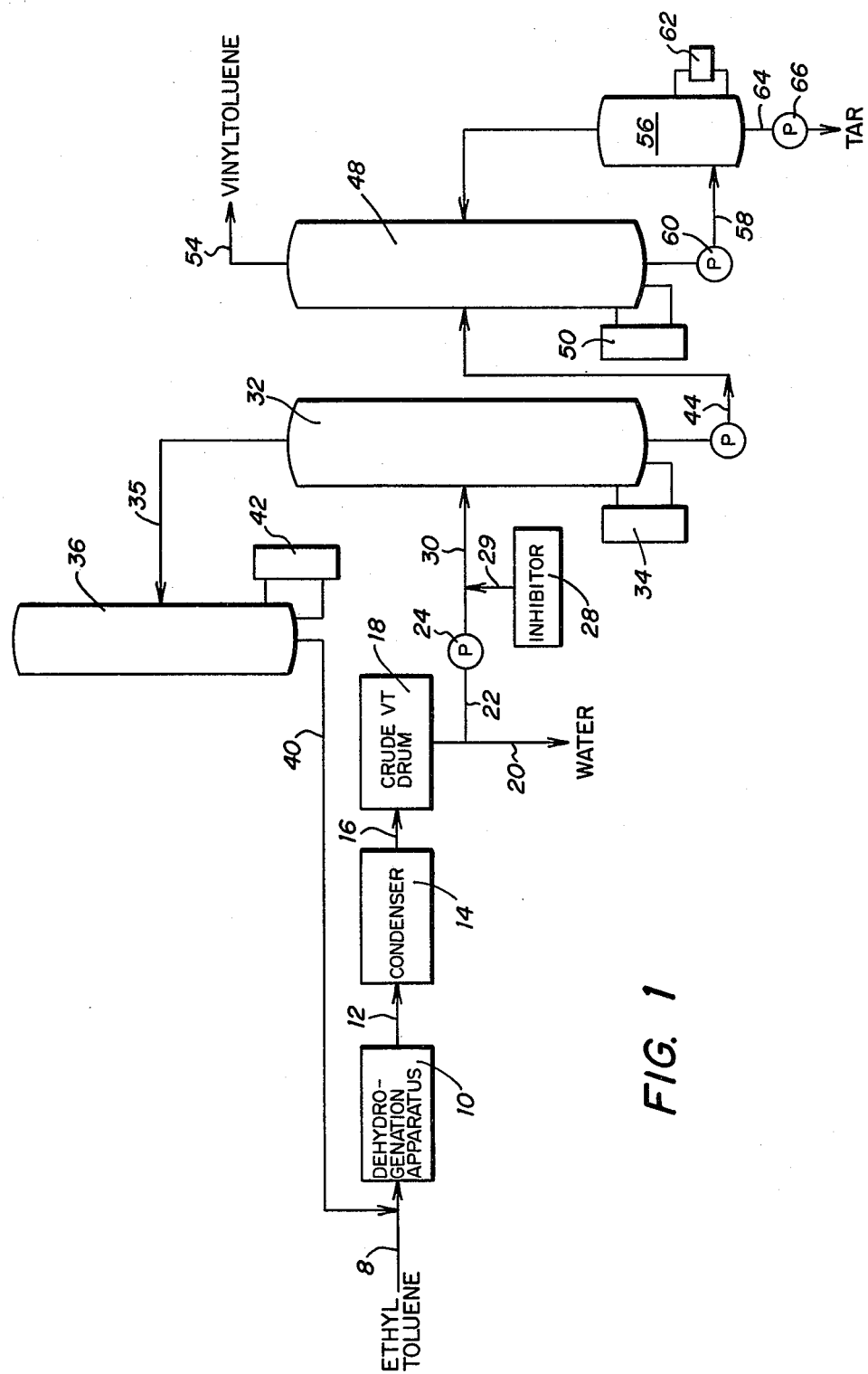
FIG. 1 is a schematic diagram of an apparatus for carrying out the process according to the present invention.

Referring to the drawings, FIG. 1 illustrates one embodiment for carrying out the process of the present invention. An ethyltoluene feedstock is introduced through line 8 into a dehydrogenation apparatus 10 to form vinyltoluene. The resulting vinyltoluene is withdrawn through line 12 and condensed in a condenser 14, then transferred via line 16 to crude vinyltoluene drum 18. Condenser 14 may comprise any of the known types of condensing equipment using air, water and/or cross exchange with another process stream to abstract heat and effect condensation.

The aqueous phase of the condensate is withdrawn from the crude vinyltoluene drum through line 20 and is recycled or returned directly to the dehydrogenation for water treatment and use in the boilers used in the dehydrogenation of ethyltoluene.

The crude vinyltoluene product remaining in the vinyltoluene drum 18 is pumped through line 22 via pump 24 into the vinyltoluene distillation train. A mixture of NDPA and DNCP from inhibitor source 28 is injected through line 29 into the vinyltoluene feedstock in line 30 and dissolved therein.

In this embodiment, the crude vinyltoluene is introduced into the intermediate portion of recycle column 32 which is preferably of parallel distillation path design. Reboiler 34 provides the necessary heat for distillation in column 32.

An overhead product comprising toluene and ethyltoluene is withdrawn through line 35 for subsequent fractionation in benzene-toluene distillation column 36. In column 36, toluene and other light distillates are separated and withdrawn through line 38. An ethyltoluene bottoms product is withdrawn through line 40 and is recycled for use in the ethyltoluene dehydrogenation reactor 10. Reboiler 42 produces the bottoms with the necessary heat for the distillation.

The recycle bottoms product, containing vinyltoluene inhibitor and polyvinyltoluene is withdrawn from the recycle column 32 through line 44 using pump 46 and is charged into the middle portion of finishing column 48. A reboiler circuit comprising a reboiler 50 is attached to the finishing column 48 for supplying the necessary heat within the column. The purified vinyltoluene overhead product is withdrawn through line 54.

The finishing column bottoms product is directed to flash pot 56 via line 58 and pump 60. The flash pot 56 has a reboiler 62 to facilitate the fractionation of the bottoms. The tar produced during the distillation process is withdrawn through line 64 by pump 66 for proper disposal.

Figure 2:
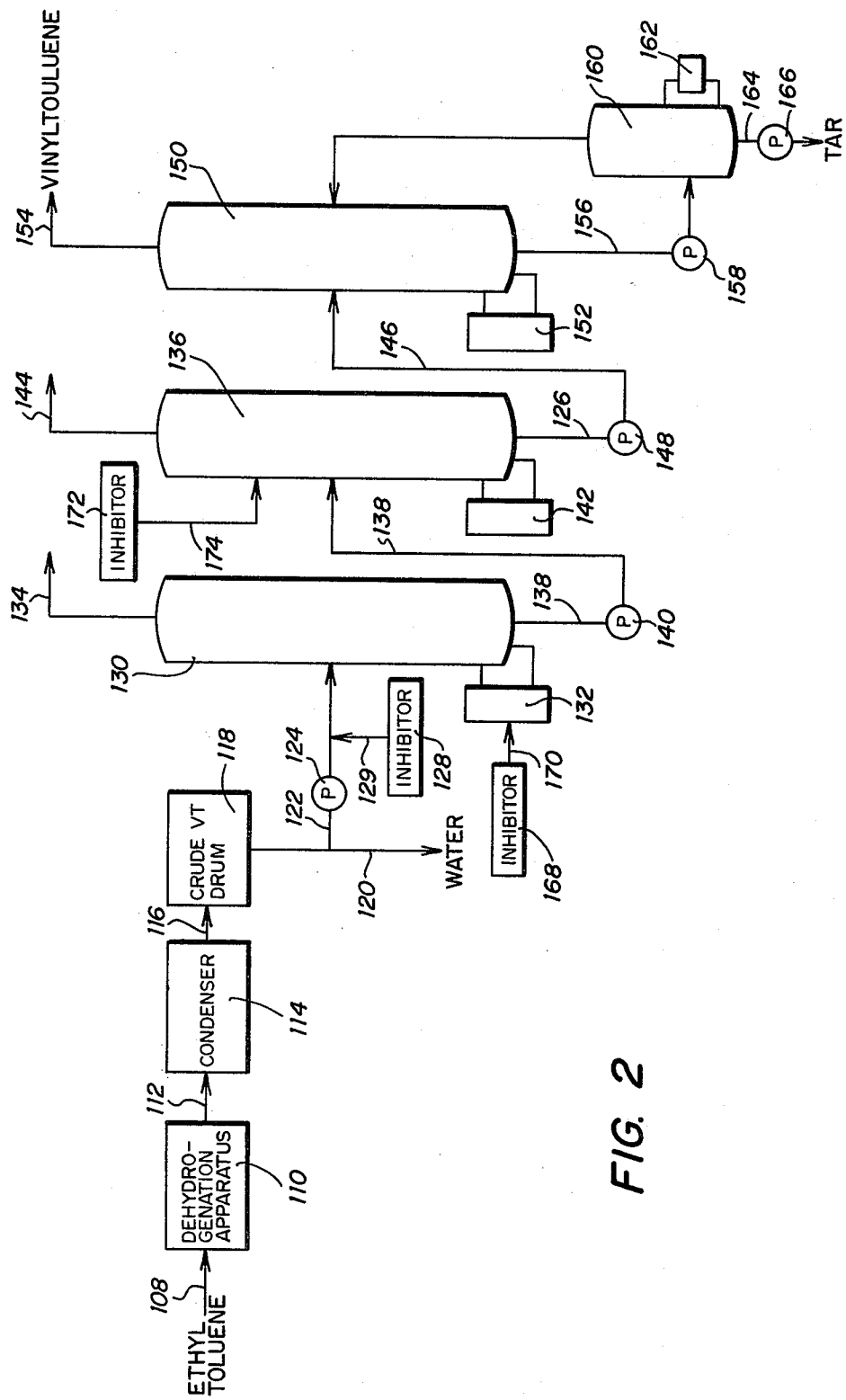
FIG. 2 is a schematic diagram of an alternate apparatus for carrying out the process of the invention.

FIG. 2 illustrates the application of the process of the present invention to another distillation train for vinyltoluene.

A polymerization inhibitor comprising a mixture of NDPA and DNPC from inhibitor source 128 is introduced through line 129 into the crude vinyltoluene flowing through feed line 122 and dissolved in the vinyltoluene feed. The inhibitor containing the crude vinyltoluene is then introduced into the intermediate portion of benzene-toluene column 130. Alternatively, the inhibitor mixture may be introduced from inhibitor source 168 through line 170 into the reboiler of benzene-toluene column 130 or from inhibitor source 172 through line 174 into the upper section of recycle column 136.

The column 130 may be of any suitable design known to those skilled in the art and may contain any suitable number of vapor-liquid contracting devices, such as bubble cap trays, perforated trays, valve trays, etc. Usually, however, column 130 contains less than 40 distillation trays. Column 130 is also equipped with a suitable reboiler 132 for supplying heat thereto.

Under the distillation conditions imposed in column 130, an overhead stream of low-boiling hydrocarbons comprising mainly toluene is removed from column 130 via line 134. These low-boiling hydrocarbons are subsequently condensed and passed into storage for further use. The bottoms product of the columns 130 is then introduced into the recycle column 136 by means of line 138 and pump 140.

The recycle column 136 may be of any suitable design known to those skilled in the art and may contain, for example, from about 40 to 100 trays. Preferably, however, the recycle column is of the parallel path design, i.e., two parallel distillation paths descending through the column. Additionally, it is also preferable that the recycle column contain a large number of trays, e.g., at least 72, in order to achieve a proper separation between the similar boiling vinyltoluene and ethyltoluene. The recycle column 136 is equipped with a suitable reboiler 142.

The ethyltoluene overhead product of the recycle column 136 is withdrawn through line 144 and is subsequently condensed for reuse in the ethyltoluene dehydrogenation apparatus 110. The recycle bottoms is withdrawn from the recycle column 136 through line 146. The recycle bottoms product is fed by pump 148 into finishing column 150 via line 146. The finishing column 150 is equipped with a reboiler 152. Inhibitor protection is adequately provided in this column and the recycle column 136 because of the prior additions of the polymerization inhibitor.

The high purity vinyltoluene overhead product is withdrawn through line 154 from the finishing column. The pure vinyltoluene product will contain greater than 99.2% by weight of vinyltoluene. The finishing column bottoms product is withdrawn through line 156 via pump 158 into flash pot 160. The flash pot 160 has a reboiler 162 to facilitate the fractionation of the bottoms. The tar produced during the distillation process is withdrawn through line 164 by pump 166 for proper disposal. However, recycling these inhibitor-bearing tars into the recycle column is also contemplated as an optional step.

During the vacuum distillation of vinyltoluene, the temperature of the reboiler is preferably maintained from about 52° C. to about 121° C. by controlling reboiler pressure at from about 30 mm to about 400 mm of Hg. Obviously, in the lower portions of the temperature and residence time ranges, small amounts of inhibitor may be utilized. Also, amounts of inhibitor greater than those specified hereinabove may be employed, although the advantages of adding the additional inhibitor are not significant and are outweighed by the corresponding increase in cost.

In the preferred embodiment, from about 100 to about 300 ppm NDPA and from about 300 to about 700 ppm DNPC are added. In the most preferred embodiment, a dosage of about 500 ppm DNPC and about 200 ppm DNPA by weight relative to the vinyltoluene present is used.

The polymerization inhibitor of the present invention may be introduced into the distillation apparatus in any convenient manner which permits efficient distribution of the inhibitor throughout the apparatus. Typically and most advantageously, the required amount of inhibitor is simply added to the reboiler area of the benzene-toluene column or to the upper section of the recycle column, although equivalent results may be obtained by incorporating the inhibitor into the incoming stream of vinylaromatic compound.

Since the inhibitor, especially the NDPA, is gradually depleted during the continuous distillation process, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. The means by which the maintenance of the necessary concentration of the inhibitor system is carried out is of no particular importance as long as the concentration of inhibitor is kept above the minimum required level.

Another factor enabling the distillation apparatus to operate at an increased rate in accordance with the present invention as opposed to conventional prior art processes is the fact that the inhibitor system of the present invention is a more efficient inhibitor at normal temperatures than the conventional inhibitors, and will thus permit higher distillation temperatures and higher pressures. In this way, the rate of distillation can be increased without increasing the amount of polymerization which has been deemed to be acceptable in accordance with conventional distillation procedures.

Upon recovery of the distillation product obtained from the process of the present invention, it is found that a higher percentage of vinyltoluene is recovered in an unpolymerized state. Moreover, the concentrated distillation residues are more easily handled and removed from the apparatus, as by pumping or the like.

In order to more fully described the present invention, the following example is presented which is intended to be merely illustrative and not in any sense limiting.

EXAMPLE

A series of experimental runs was made to demonstrate the effectiveness of the present inhibitor system. In these runs, crude vinyltoluene was purified under vacuum distillation conditions. The inhibitor used was a mixture of 200 ppm of NDPA by weight and 500 ppm by weight of NDPC. After the test runs, the distillation columns of the distillation apparatus were examined. Only negligible amounts of polymerized material were found in the distillation columns. This was true even of areas exposed to low velocity vapors, such as the undersides of the seal pans, where polymer accumulations usually form.

For comparison purposes a second series of test runs was thereafter carried out using conventional polymerization inhibitors under vacuum distillation conditions to purify the crude vinyltoluene. After the second series of test runs were completed, the distillation columns of the distillation apparatus were again examined. The distillation columns were found to be fouled with substantial accumulations of polymerized material. Insoluble polymer accumulations were particularly evident on the bottoms of the seal pans. Cleaning of the columns was required before the columns could be reused.

The foregoing embodiments have been described solely for purposes of exemplification and are not intended to be limiting. Since modifications of the disclosed embodiments incorporating the substance and spirit of the invention may occur to persons skilled in the art, the scope of the invention is to be limited solely by the scope of the appended claims.

What is claimed is:

1. A process for the distillation of vinyltoluene comprising subjecting said vinyltoluene to distillation conditions in the presence of an effective polymerization inhibiting amount of a polymerization inhibitor mixture comprising dinitro-p-cresol and N-nitroso-diphenylamine.

2. The process of claim 1, wherein said distillation conditions comprise vacuum distillation conditions.

3. The process of claim 1, wherein said mixture of dinitro-p-cresol and N-nitrosodiphenylamine is present in an amount of from about 200 ppm to about 1000 ppm.

4. The process of claim 1, wherein the temperature of said distillation is between about 52° C. to 121° C.

5. The process of claim 1, wherein the amount of dinitro-p-cresol used is from about 300 to about 700 ppm and the amount of N-nitrosodiphenylamine used is from about 100 to about 300 ppm by weight relative to the vinyltoluene present.

6. The process of claim 1, wherein the amount of dinitro-p-cresol used is about 500 ppm, and the amount of N-nitrosodiphenylamine is about 200 ppm by weight relative to the vinyltoluene present.

* * * * *